United States Patent
Ridell et al.

(10) Patent No.: US 12,421,134 B2
(45) Date of Patent: Sep. 23, 2025

(54) SYSTEM FOR WATER QUALITY MEASUREMENT AND A RECIRCULATION SYSTEM COMPRISING THE SAME

(71) Applicant: Orbital Systems AB, Malmö (SE)

(72) Inventors: Michael Ridell, Staffanstorp (SE); Richard Boden, Malmö (SE); Peter Öhman, Staffanstorp (SE)

(73) Assignee: Orbital Systems AB, Malmö (SE)

( * ) Notice: Subject to any disclaimer, the term of this patent is extended or adjusted under 35 U.S.C. 154(b) by 415 days.

(21) Appl. No.: 18/011,466

(22) PCT Filed: Jun. 23, 2021

(86) PCT No.: PCT/SE2021/050616
§ 371 (c)(1),
(2) Date: Dec. 19, 2022

(87) PCT Pub. No.: WO2021/262072
PCT Pub. Date: Dec. 30, 2021

(65) Prior Publication Data
US 2023/0322582 A1 Oct. 12, 2023

(30) Foreign Application Priority Data
Jun. 26, 2020 (SE) .................... 2050774-5

(51) Int. Cl.
*C02F 1/00* (2023.01)
*E03B 1/04* (2006.01)
(Continued)

(52) U.S. Cl.
CPC .............. *C02F 1/008* (2013.01); *E03B 1/041* (2013.01); *E03C 1/22* (2013.01); *E03F 5/0408* (2013.01);
(Continued)

(58) Field of Classification Search
CPC ............... C02F 1/008; C02F 2103/002; C02F 2201/007; C02F 1/001; E03B 1/041;
(Continued)

(56) References Cited

U.S. PATENT DOCUMENTS 3,250,118 A * 5/1966 Johnson, Jr. ........... G01N 33/18
422/82.12
11,452,951 B2 * 9/2022 Oscarson ............. B01D 27/146
(Continued)

FOREIGN PATENT DOCUMENTS

CA 2794457 A1 * 10/2011 ............. E03B 7/045
CN 101579198 B 6/2011
(Continued)

OTHER PUBLICATIONS

English translation of patent publication CN 107664350, published Feb. 6, 2018 . (Year: 2018).*
(Continued)

*Primary Examiner* — Joseph W Drodge
(74) *Attorney, Agent, or Firm* — NovoTechIP International PLLC

(57) ABSTRACT

The present invention refers to a system 1 intended for measuring water quality in a system having the capability of recirculating water and flowing water to waste, depending on water quality, said system 1 being a module system comprising a water channel base unit 2, a sensor module unit 3 for water quality measurement and a water distribution module unit 4 for distribution of water to recirculation, wherein the water distribution module unit 4 are attachable to and detachable from the water channel base unit 2.

18 Claims, 1 Drawing Sheet

(51) Int. Cl.
- *E03C 1/22* (2006.01)
- *E03F 5/04* (2006.01)
- *G01N 1/20* (2006.01)
- *G01N 33/18* (2006.01)
- *C02F 103/00* (2006.01)

(52) U.S. Cl.
CPC ............... *G01N 1/20* (2013.01); *G01N 33/18* (2013.01); *C02F 2103/002* (2013.01); *C02F 2201/007* (2013.01)

(58) Field of Classification Search
CPC ........ E03B 1/042; E03C 1/22; E03C 2201/40; E03F 5/0408; E03F 5/0407; A47K 3/28; A47K 3/40; A47K 3/405; G01N 1/10; G01N 1/20; G01N 2001/1031; G01N 33/18; G01N 33/1886; G01N 33/1893
See application file for complete search history.

(56) References Cited

U.S. PATENT DOCUMENTS

| | | | | |
|---|---|---|---|---|
| 12,018,467 | B2 * | 6/2024 | Öbrink | ................ F24D 19/1051 |
| 12,134,568 | B2 * | 11/2024 | Mahdjoubi Namin | . C02F 1/008 |
| 2002/0189173 | A1 * | 12/2002 | Staschik | ................. F02G 1/043 |
| | | | | 52/79.1 |
| 2011/0067769 | A1 * | 3/2011 | Stimpson | ................ E03D 5/003 |
| | | | | 137/565.01 |
| 2011/0146800 | A1 * | 6/2011 | Jallon | ....................... C02F 9/20 |
| | | | | 4/597 |
| 2014/0116553 | A1 * | 5/2014 | Schoolcraft | ............. E03C 1/057 |
| | | | | 137/801 |
| 2016/0289087 | A1 * | 10/2016 | Yagita | .................... G01N 33/18 |
| 2018/0201516 | A1 | 7/2018 | Mahdjoubi et al. | |
| 2018/0362367 | A1 * | 12/2018 | Mahdjoubi Namin | ...................... E03B 7/074 |
| 2020/0087898 | A1 * | 3/2020 | Spiro | ...................... E03B 1/041 |
| 2020/0318323 | A1 * | 10/2020 | Pendlebury | ............. E03B 1/044 |
| 2022/0170264 | A1 * | 6/2022 | Badin Cherit | .......... E04C 5/065 |
| 2023/0117729 | A1 * | 4/2023 | Dennbo | .................. F16L 9/147 |
| | | | | 137/563 |

FOREIGN PATENT DOCUMENTS

| | | | | |
|---|---|---|---|---|
| CN | 107664350 | A * | 2/2018 | |
| DE | 102008046671 | A1 | 6/2009 | |
| EP | 2962612 | A1 | 1/2016 | |
| GB | 2545399 | A * | 6/2017 | ............... A47K 3/28 |
| WO | 2013095278 | A1 | 6/2013 | |
| WO | 2019164436 | A1 | 8/2019 | |
| WO | 2020112001 | A1 | 6/2020 | |
| WO | 2020112002 | A1 | 6/2020 | |
| WO | WO-2020256536 | A1 * | 12/2020 | ............... E04B 2/18 |

OTHER PUBLICATIONS

International Search Report and Written Opinion issued Aug. 20, 2021 in corresponding PCT/SE2021/050616.

* cited by examiner

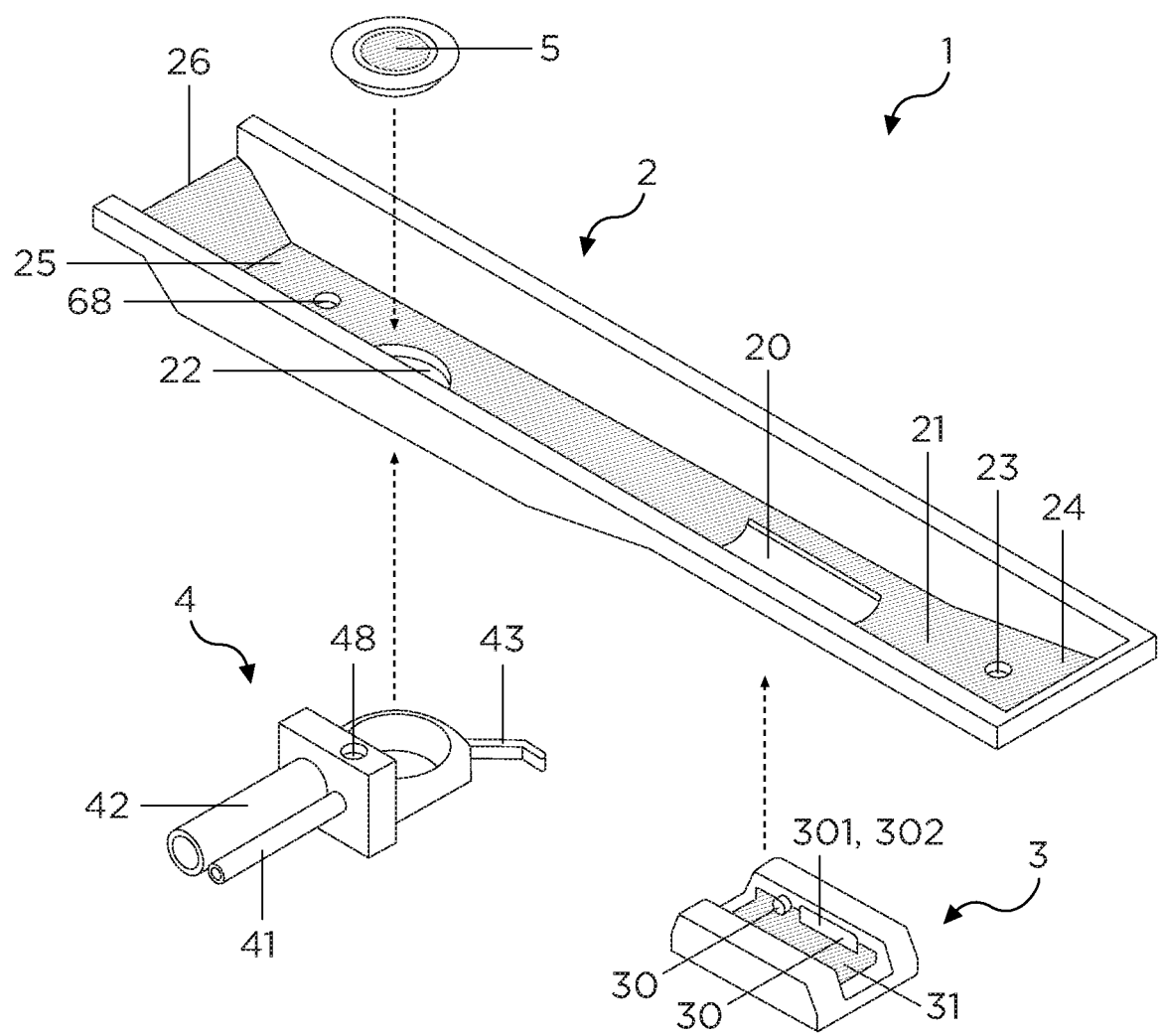

SYSTEM FOR WATER QUALITY MEASUREMENT AND A RECIRCULATION SYSTEM COMPRISING THE SAME

FIELD OF THE INVENTION

The present invention relates to a system for water quality measurement, especially such a system intended for water recirculation systems, e.g. a recirculating shower.

TECHNICAL BACKGROUND

Water recirculation system, such as recirculating showers are known. For instance, in WO 2013/095278 there is disclosed a hybrid device for a recirculation shower, allowing purification and either recycling of water or discarding of water, wherein said hybrid device comprises a recirculation loop, a filter system with a nano-filter such as for instance an electropositive nano-ceramic filter, e.g. a nano alumina (fiber) filter, at least one filter quality sensor, at least one pre-filter, and wherein the hybrid device is arranged to redirect the water from recirculation to drainage when the at least one filter quality sensor indicates the need thereof. According to one embodiment, said hybrid device is said to comprise a modified drain. The modified drain collects the water used and facilitates the stream of water towards the recycling loop and filter system or towards drainage. The modified drain may comprise at least one sensor, indicating the water quality, and where the hybrid device is arranged to redirect the water from recirculation to drainage when the at least one water quality sensor indicates the need thereof. Said water quality sensor may be a TOC sensor (Total Organic Carbon), a biosensor, a pH meter (measuring acidity or alkalinity) or an optical sensor, but also other kinds of similar means are possible.

The present invention is directed to a system for measuring water quality, e.g. in water recirculation systems, such as a recirculating shower. The system according to the present invention is directed to a unit which provides an improved and simplified installation of a water quality measurement unit in water recirculation systems. Moreover, the present invention also provides an increased flexibility when used in different types of technical applications. Furthermore, the present invention also implies other advantages, which will become clear below.

SUMMARY OF THE INVENTION

The stated purpose above is achieved by a system intended for measuring water quality in a system having the capability of recirculating water and flowing water to waste, depending on water quality, said system being a module system comprising a water channel base unit, a sensor module unit for water quality measurement and a water distribution module unit for distribution of water to recirculation, wherein the water distribution module unit are attachable to and detachable from the water channel base unit.

As notable from above, the system according to one aspect of the present invention is a module based system. This has several advantages. First of all, a great flexibility is obtained when producing the dockable module system according to the present invention. The module system may be provided with different types of sensor module units to adapt the system to different types of applications. Secondly, also the user will experience an improved flexibility and user-friendliness. As also the water distribution module unit is module based this part is much more simple to remove and clean etc. if needed, also for the installation procedure. In this regard it may also be mentioned that the sensor module unit is intended to be fixated already during the production assembly. These parts are then not intended to be removed from each other once they have been connected. The water distribution module unit, however, is intended to be connected during the installation procedure. Moreover, this unit may also be disassembled by the user or by suitable operators after installation.

Moreover, another benefit of the module system according to the present invention is also that a dockable sensor module unit enables a better basis to ensure to protect electric components, such as wires etc. drawn from sensors of the sensor module unit. All these fragile parts may be provided beneath the entire system according to the present invention. Only the sensor(s) have to have a direct contact with the water flow. This may be understood when viewing the FIGURE.

According to another aspect of the present invention, there is provided a system intended for measuring water quality in a system having the capability of recirculating water and flowing water to waste, depending on the water quality, said system comprising a water channel base unit, a sensor module unit for water quality measurement and a water distribution module unit for distribution of water to recirculation, wherein the water channel base unit comprises a channel comprising a recirculation drain hole, and wherein the water distribution module unit comprises a water recirculation connection arranged to suck water into recirculation from the channel, preferably from below the channel.

Also this aspect of the present invention has several advantages. By sucking water from below, the obtained water column is utilized in an optimal way. This in turn prevents air to be sucked into the water recirculation flow, which is of importance for the entire system, pump etc.

Moreover, to enable flushing of the water channel is also of interest. This is of interest to enable flushing of debris to waste, e.g. instead of such getting stuck in the filter (explained below). Moreover, a flushing function also keeps the water channel in a better condition, which in turn may have a positive effect on sensors and other units. In line with this, according to one specific embodiment, the water distribution module unit comprises two connections which are a channel spraying connection and a water recirculation connection, wherein the water channel base unit is provided with spraying holes which are connected to the channel spraying connection via a connection point of the water distribution module unit, preferably via a channel network being a part of the water channel base unit.

Moreover, as is evident from above, according to one specific embodiment of the present invention, the water distribution module unit comprises two connections.

Furthermore, the spraying holes enables to flush the water channel to send debris, hair and the like to waste. Such a flushing functionality may also ensure to keep a filter unit arranged over a drain hole of the channel of the water channel, which is the flow route to recirculation, in a clean mode. This is of importance to ensure the correct water flow level without clogging. Such a filter is explained in more detail below. In this regard it should be noted that it may also be of interest to enable to shift the flow direction and create a flow through the filter unit if any material has clogged the filter and cannot be flushed away by flushing the water channel.

The present system may also be arranged with other units affecting the water flow. One such is one or more so called vortex preventers. Such a unit prevents a vortex to be formed in the water flow going into the recirculation line. Again, also this add-on may be arranged to ensure that air is prevented to be sucked into the recirculation line and pump etc.

Other details and benefits are presented below in relation to certain embodiments etc.

SPECIFIC EMBODIMENTS OF THE INVENTION

Below specific embodiment of the present invention are disclosed and discussed further.

According to a first aspect of the present invention, the system is a module system. Therefore, according to one embodiment, the water distribution module unit are attachable to and detachable from the water channel base unit.

According to yet another specific embodiment of the present invention, and as stated above, the sensor module unit is arranged to be attachable to the water channel base unit during the production of the module system. When a certain type of sensor module unit is decided for the system, then this may be integrated into the system and electric wires etc. are connected.

According to yet another specific embodiment of the present invention, the sensor module unit is attachable into a hole of a channel of the water channel base unit so that at least one sensor of the sensor module unit is arranged inside along the channel of the water channel base unit. This type of arrangement implies that although a module capability is provided, the arrangement of the sensor(s) will still be such as they were in a fixed installation. This further implies that both flexibility and stability is provided by the sensor module system according to the present invention.

The type of sensors used in the system according to the present invention may vary. According to one specific embodiment of the present invention, the sensor module unit comprises a channel with two opposite sensors, which channel matches the channel of the water channel base unit when the sensor module unit is connected into the hole of the water channel base unit. As should be understood from above, according to this embodiment, opposite sensors may be of different types, e.g. one EC sensor and one turbidity sensor, or may be of the same type. Other possible sensor types that may be integrated in a system according to the present invention are one or more LED sensors (e.g. for turbidity measurement), temperature sensors, or colour sensors. Moreover, the sensors may be used for different types of measurements, such as water level, water quality, temperature etc.

The sensor module system according to the present invention is intended to enable water quality measurement when at the same time also enable distribution of water to and from the sensor module system. According to one specific embodiment of the present invention, the water distribution module unit is connectable to and detachable from a recirculation drain hole of the channel of the water channel base unit. This recirculation drain hole (or holes) is the recirculation outflow from the sensor module system.

Furthermore, according to yet another specific embodiment of the present invention, a filter unit is connectable to and detachable from a recirculation drain hole of the channel of the water channel base unit. The filter unit may have several tasks or features. First of all, the filter unit of course acts as a filter to ensure that large particles, hair or debris do not enter into the recirculation but instead is flushed to waste. Moreover, the filter unit may also act as the "locking" unit for the entire water distribution module unit. This may have a certain "clipping function" or the like. Therefore, according to yet another specific embodiment of the present invention, the water distribution module unit is connectable to and detachable from the filter unit, and wherein the distribution module unit and the filter unit fixate the channel between the filter unit and the water distribution module unit. Furthermore, the water distribution module unit may also comprise means for locking and unlocking of the water distribution module unit. This functionality may be arranged to enable to lock the position of the module unit into the entire mounting or structure, such as the floor armature.

Moreover, the water distribution module unit and sensor module unit may have common units when being arranged into the system. Moreover, these two modules may also be connected to each other before being integrated into the water channel base unit.

The water distribution module unit may also have several tasks and features. As mentioned, according to one specific embodiment of the present invention, the water distribution module unit comprises two connections. A water recirculation system may comprise a core which is connected to the system according to the present invention. The two connections mentioned above are one on the pressure side connected to the core and another one the suction side from the core.

Furthermore, the system according to the present invention may also have an internal flushing functionality, as explained above.

As mentioned above, water with an enough quality level is intended to be recirculated, however water with a quality level below a certain level is sent to waste. To enable this, the system according to the present invention should have a route for sending water to waste, e.g. an overflow arrangement as mentioned below. According to one embodiment of the present invention, a channel of the water channel base unit has two ends, one first end arranged for water inflowing and one second end comprising an overflow arrangement which is arranged to send water to waste.

Furthermore, also other units may be connected to a system according to the present invention. As an example, according to one specific embodiment of the present invention, one of the connections is a core water recirculation unit connection which is connected to a water tank of a core unit of a water recirculation system.

Furthermore, and as should be understood from above, according to yet another specific embodiment of the present invention, the system is arranged in a drain of a water recirculation system having the ability to send water of lower quality to waste and recirculate water of higher quality, based on measurement of water quality. Therefore, the present invention also refers to a water recirculation system comprising the system according to the present invention and as is described above.

DETAILED DESCRIPTION OF THE DRAWINGS

In FIG. 1 there is shown a system 1 according to one embodiment of the present invention, in the form of a module system 1. The module system 1 is intended for measuring water quality in a system having the capability of recirculating water or flowing water to waste. Moreover, the module system 1 comprises a water channel base unit 2, a sensor module unit 3 and a water distribution module unit 4, and the water distribution module unit 4 are attachable to and detachable from the water channel base unit 2.

According to this embodiment, the sensor module unit 3 is attachable into a hole 20 of a channel 21 of the water channel base unit 2 so that at least one sensor 30 of the sensor module unit 3 is arranged inside along the channel 21 of the water channel base unit 2. In this case, the sensor module unit 3 comprises a channel 31 with two opposite sensors 301, 302, and the channel 31 matches the channel 21 of the water channel base unit 2 when the sensor module unit 3 is connected into the hole 20 of the water channel base unit 2.

Furthermore, it may also be said that the water channel base unit 2 may be provided with a geometrical narrowing ensuring to keep a high enough water level for the sensors. This is not shown in the embodiment shown in the FIGURE.

Moreover, electrical wire connections between the sensor module unit 3 and to the sensors units 30 (301, 302) are also provided, however not shown. Furthermore, such wires are also provided from the sensor module unit 3 and to a control unit or the like for the entire system having the capability of recirculating water or flowing water to waste (also not shown). Such wiring is arranged into the system during the production thereof.

Moreover, in this case the water distribution module unit 4 is connectable to and detachable from a recirculation drain hole 22 of the channel 21 of the water channel base unit 2. Furthermore, a filter unit 5 is connectable to and detachable from the recirculation drain hole 22. Moreover, the filter unit 5 may have wings (not shown) which are intended to affect the water flow. Moreover there may also be an extra spraying hole (not shown) of the water channel base unit 2, which is provided in close connection to the filter unit/mesh 5. Such an extra spraying hole may have the purpose of enabling to free the filter unit 5 from debris, hair etc.

Furthermore, as notable, the water distribution module unit 4 comprises two connections 41, 42. Both these connections are intended to be connected to a core unit of a recirculating shower. The connection 41 is a flushing tube, i.e. an outlet, enabling to flush water to spraying holes 23 arranged at different places inside the water channel base unit 2. This connection 41 is provided on the pressure side of the core and pump. Furthermore, the connection 42 is a recirculation tube, i.e. an inlet, intended for recirculation of water inside of a recirculating shower. This connection 42 is provided on a suction side of the core.

Moreover, and as hinted above, the water channel base unit 2 is provided with spraying holes 23 (only one shown, but several may be provided) which are connected to a channel spraying connection 41 via a connection point 48 of the water distribution module unit 4, preferably via a channel network being a part of the water channel base unit 2.

Furthermore, a channel 21 of the water channel base unit 2 has two ends 24, 25, one first end 24 arranged for water inflowing and one second end 25 comprising an overflow arrangement 26 which is arranged to send water to waste.

Moreover, in this case there is an extra small drain hole 68 arranged at the second end 25. This may be arranged to ensure that water is not standing still in this end also after the drain hole 22.

Moreover, the end 25 and overflow arrangement 26 may have different shapes, and not only the shape provided in the FIGURE. As an example, the end shape may be curved. Furthermore, there may also be arranged a countersink in the middle of the overflow arrangement 26 to ensure a better draining off in the overflow.

In addition, the water distribution module unit 4 comprises means 43 for locking and unlocking of the water distribution module unit 4. It should be noted that the locking means 43 may be provided in many different ways, e.g. as a separate unit being fixated onto the water distribution module unit 4.

The invention claimed is:

1. A water quality measuring system configured for measuring water quality in a water recirculation system having capabilities of recirculating water and flowing water to waste, based on the water quality measured by the water quality measuring system, said water quality measuring system being a module system comprising a water channel base unit, a sensor module unit, attached to the water channel base unit for water quality measurement, and a water distribution module unit for distribution of water to recirculation, wherein;

the water distribution module unit is configured to be attachable to and detachable from the water channel base unit, and the sensor module unit is attachable into a hole of a channel of the water channel base unit so that at least one sensor of the sensor module unit is arranged in communication with water in the channel of the water channel base unit via the hole of the channel.

2. The water quality measuring system according to claim 1, wherein the water distribution module unit comprises two connections which are a channel spraying connection and a water recirculation connection, wherein the water channel base unit is provided with spraying holes which are connected to the channel spraying connection via a connection point of the water distribution module unit and via a channel network being a part of the water channel base unit.

3. The water quality measuring system according to claim 1, wherein the sensor module unit is arranged to be attachable to the water channel base unit before completion of the water quality measuring system.

4. A water quality measuring system configured for measuring water quality in a water recirculation system having capabilities of recirculating water and flowing water to waste, based on the water quality measured by the water quality measuring system, said water quality measuring system comprising a water channel base unit, a sensor module unit, attached to the water channel base unit for water quality measurement, and a water distribution module unit for distribution of water to recirculation, wherein:

the water channel base unit comprises a channel which includes a recirculation drain hole, and the sensor module unit is attachable into a hole of the channel of the water channel base unit, different than the recirculation drain hole, so that at least one sensor of the sensor module unit is arranged in communication with water in the channel of the water channel base unit via the hole of the channel.

5. The water quality measuring system according to claim 4, wherein the water distribution module unit is both attachable to and detachable from the water channel base unit.

6. The water quality measuring system according to claim 4, wherein the sensor module unit comprises a sensor channel with a first sensor on one side of the sensor channel and a second sensor on an opposite side of the sensor channel, facing the first sensor with the sensor channel interposed between the first and second sensors, wherein the sensor channel is aligned with the channel of the water channel base unit.

7. The water quality measuring system according to claim 4, wherein the water distribution module unit is connectable to and detachable from the recirculation drain hole of the channel of the water channel base unit.

8. The water quality measuring system according to claim 4, wherein a filter unit is connectable to and detachable from the recirculation drain hole of the channel of the water channel base unit.

9. The water quality measuring system according to claim 8, wherein the water distribution module unit is connectable to and detachable from the filter unit, and wherein the distribution module unit and the filter unit secure the channel between the filter unit and the water distribution module unit.

10. The water quality measuring system according to claim 4, wherein the water distribution module unit includes a core water recirculation unit connection which is connected to a water tank of the water recirculation system.

11. The water quality measuring system according to claim 4, wherein the water distribution module unit comprises means for locking and unlocking of the water distribution module unit to the water channel base unit.

12. The water quality measuring system according to claim 1, wherein the system is arranged in a drain of the water recirculation system to send water having a water quality below a predetermined threshold to waste and to recirculate water having a water quality above the predetermined threshold, based on measurement of water quality by the water quality measuring system.

13. A water recirculation system comprising the water quality measuring system according to claim 1.

14. A water recirculation system comprising the water quality measuring system according to claim 4.

15. The water quality measuring system according to claim 4, wherein the water distribution module unit comprises a channel spraying connection and a water recirculation connection, wherein the water channel base unit is provided with spraying holes which are connected to the channel spraying connection via a connection point of the water distribution module unit and via a channel network being a part of the water channel base unit.

16. The water quality measuring system according to claim 4, wherein the water distribution module unit comprises a water recirculation connection arranged to perform the recirculating of water by sucking water from below the channel.

17. A water quality measuring system configured for measuring water quality in a water recirculation system having capabilities of recirculating water and flowing water to waste, based on the water quality measured by the water quality measuring system, said water quality measuring system comprising a water channel base unit, a sensor module unit, attached to the water channel base unit for water quality measurement, and a water distribution module unit for distribution of water to recirculation, wherein:
- the water channel base unit comprises a channel comprising a recirculation drain hole; and
- the channel of the water channel base unit has a first end arranged for water inflowing and a second end comprising an overflow arrangement which is arranged to send water to waste.

18. The water quality measuring system according to claim 17, wherein the water distribution module unit comprises a water recirculation connection arranged to perform the recirculating of water by sucking water from below the channel.

* * * * *